United States Patent [19]

Josefsen et al.

[11] 4,123,701
[45] Oct. 31, 1978

[54] DISPOSABLE SAMPLE CARD HAVING A WELL WITH ELECTRODES FOR TESTING A LIQUID SAMPLE

[75] Inventors: Turi L. H. Josefsen, New York, N.Y.; George J. Veth, Fairfield, Conn.

[73] Assignee: United States Surgical Corporation, Stamford, Conn.

[21] Appl. No.: 701,885

[22] Filed: Jul. 1, 1976

[51] Int. Cl.² ............................................. G01N 27/42
[52] U.S. Cl. ................................ 324/30 B; 324/65 R; 128/2 G; 128/2.1 E
[58] Field of Search ................ 324/30 B, 30 R, 65 R; 128/2 G, 2.1 E, 2 F; 424/11, 12; 23/230 B, 253 TP

[56] References Cited

U.S. PATENT DOCUMENTS

| | | | |
|---|---|---|---|
| 2,555,937 | 6/1951 | Rosenthal et al. | 324/30 B |
| 3,250,987 | 5/1966 | Okada et al. | 324/30 B |
| 3,376,501 | 4/1968 | Peranio | 324/30 B |
| 3,743,581 | 7/1973 | Cady et al. | 324/30 B X |
| 3,781,659 | 12/1973 | Ur | 324/30 B |
| 3,840,806 | 10/1974 | Stoner et al. | 324/65 R |
| 3,919,627 | 11/1975 | Allen | 324/30 R |
| 3,980,946 | 9/1976 | Fleury | 324/30 B X |
| 3,990,850 | 11/1976 | Friedman et al. | 23/230 B |

*Primary Examiner*—Robert J. Corcoran
*Attorney, Agent, or Firm*—Fleit & Jacobson

[57] ABSTRACT

Disclosed are several embodiments of a disposable sample card for testing fluids such as blood and the like. A generally planar card contains a chamber, or well and supports two insulated electrodes which terminate in the region of the well. Various electrode configurations are disclosed, each adapted to associate with an instrument for applying an electric voltage between the two electrodes, and across the sample under study. Also disclosed is an instrument for receiving the specially shaped sample cards.

21 Claims, 7 Drawing Figures

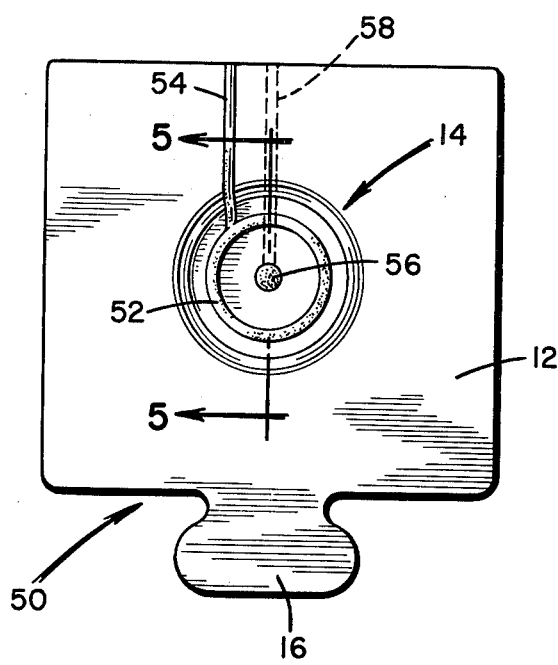
FIG. 4
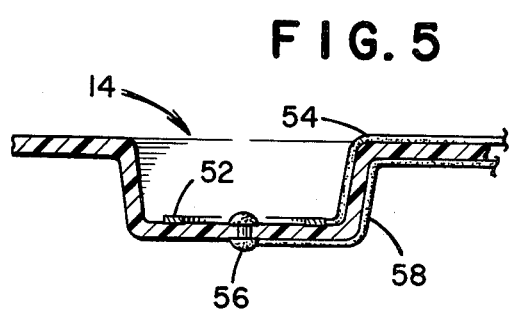
FIG. 5
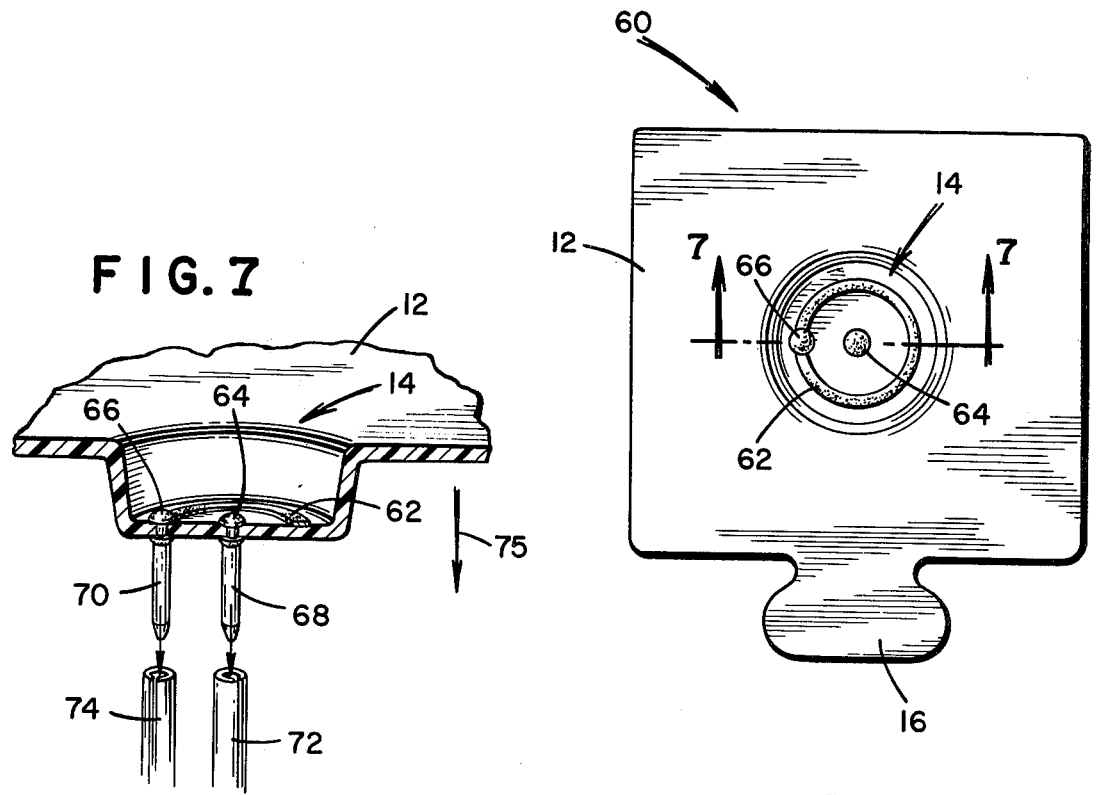
FIG. 7
FIG. 6

DISPOSABLE SAMPLE CARD HAVING A WELL WITH ELECTRODES FOR TESTING A LIQUID SAMPLE

BACKGROUND OF THE INVENTION

The present invention relates generally to the field of sample testing, and is specifically adapted to medical studies of body fluid samples, particularly blood, and to testing various parameters of blood such as the making of hematocrit determinations. More particularly, the invention relates to the study of body fluid samples by evaluating the electrical properties of such samples.

Various methods and apparatus are known for studying liquid samples. Some involve centrifucation, others utilize agitation, and there are still others which depend upon the electrical characteristics of the sample being tested. In virtually all of these known techniques, especially those in the medical field, it is of prime importance to maintain isolation between samples. Careful scrubbing and the use of an autoclave between successive tests are generally sufficient to eliminate cross-contamination of samples. Yet the possibility of contamination still remains.

A further problem relates to the protection of the technician against contracting infectious diseases from the samples under test. With the known methods and apparatus, very little protection if afforded.

An example of an apparatus for studying the electrical characteristics of blood can be found in U.S. Pat. No. 3,922,598, issued to Steuer et al. on Nov. 25, 1975. This apparatus includes a rod-like probe having two conductive electrodes at the tip of the probe. A blood sample is associated with the electrodes of the probe, and an electric voltage is applied across the blood for the purpose of hematocrit determinations. Obviously, the probe must be thoroughly cleaned between tests to ensure accurate test results.

It is toward the accomplishment of a simplified, safe and accurate electrical evaluation of liquid samples that the present invention is directed.

SUMMARY OF THE INVENTION

The present invention relates generally to sample testing by electrical means. Particular use is found for the invention in the medical field, especially in studying the electrical conductivity of whole blood samples and the like.

Specifically, the present invention takes the form of a disposable card containing a chamber, or well, and supporting a pair of electrical contacts in the region of the well. In use, the well is filled with a test fluid, such as whole blood, and the disposable card is associated with an instrument which passes an electric current through the test sample to determine its conductance, and hence the characteristic under study.

In one embodiment, both electrodes are plated on the top surface of the card. The first electrode terminates in a button centrally positioned at the bottom of the well. The second electrode, also located in the bottom of the well, surrounds the first, interrupted only to permit the lead of the first electrode to enter the central region of the well. The opposite ends of the electrode leads terminate at an edge of the card for connection to conventional printed circuit terminals.

A second embodiment of the inventive card has a central electrode similar to that of the first embodiment, but entering the well through the bottom surface of the card. The other electrode is plated on the top of the card, and forms a complete ring about the central button electrode in the well. The electrode leads associate with printed circuit terminals as previously described.

In a third embodiment, the central electrode takes the form of a button entering the well from the bottom surface of the card, and the other electrode takes the form of an outer concentric ring, the lead of which also enters the well from beneath the card. Connector pins extend downwardly from both electrodes, under the well, and are there adapted to mate with appropriate conventional connectors. These may take the form of female sockets if the card is received from the top, or resilient spring clips to receive the card if introduced in the plane of its base.

The inventive sample-receiving cards are disposable, so that after one sample has been tested, the soiled card is dispensed with and replaced by a new card for the next sample. This procedure eliminates the possibility of cross-contamination of samples, and minimizes the chances of the technician contracting disease from the sample.

The cards are packaged in a clean and uncontaminated condition, are handled by a small finger tab, and therefore also cure the contamination and cleaning difficulties of prior art techniques.

The present invention also relates to an instrument having a special casing design for receiving the inventive sample cards. This instrument includes a guide and support for guiding sample cards into the instrument, for supporting the cards in the instrument and for associating the cards with appropriate electrical circuitry.

It is accordingly a principal object of the present invention to provide a mechanism whereby a liquid sample can be tested by electrical means in an efficient and reliable manner.

A more specific object of the present invention is to provide disposable sample cards for receiving liquid samples and for determining a characteristic of such samples through electrical means.

A further object of the present invention is to provide a technique for testing body fluids in a manner which avoids cross-contamination of samples and which minimizes the possibility of a technician contracting a disease.

Another specific object of the present invention is to provide disposable sample receptacles for electrical evaluations of body fluids, such as hematocrit determinations.

Another object of the present invention is to provide an instrument particularly suited to receive the inventive disposable sample cards.

These and other objects of the present invention, as well as many of the attendant advantages thereof, will become more readily apparent when reference is made to the following description, taken in conjunction with the accompanying drawings.

BRIEF DESCRIPTION OF THE DRAWINGS

FIG. 4 is a top plan view illustrating a second embodiment of the inventive sample card;

FIG. 5 is a cross-section of the inventive card, taken along line 5—5 of FIG. 4;

FIG. 6 is a top plan view of still another embodiment of the inventive sample card; and FIG. 7 is a cross-section of the inventive card taken along line 7—7 of FIG. 6, also showing connector sockets.

DETAILED DESCRIPTION OF THE DRAWINGS

Figure 3:
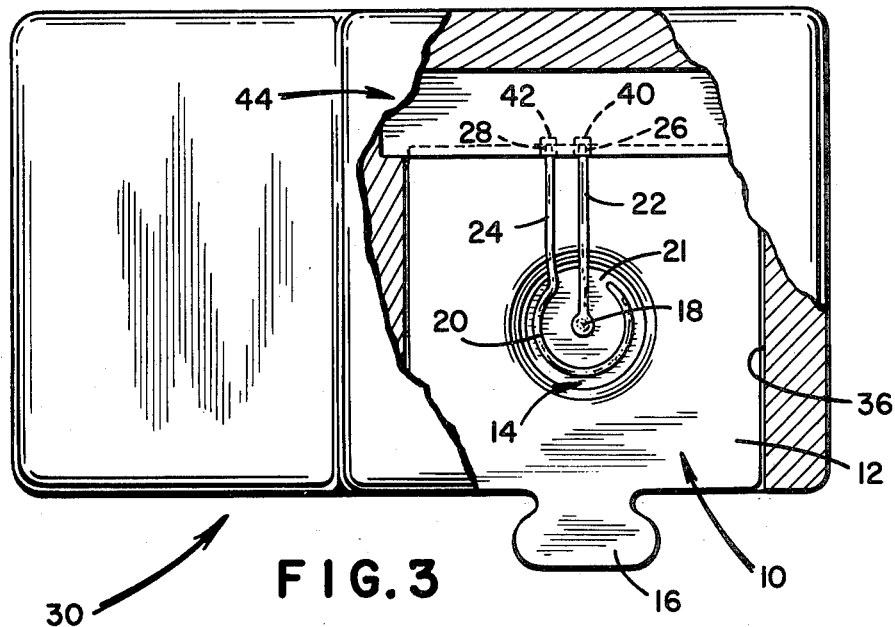
FIG. 3 is a top view, partially broken away, of the instrument illustrated in FIG. 2.
Figure 2:
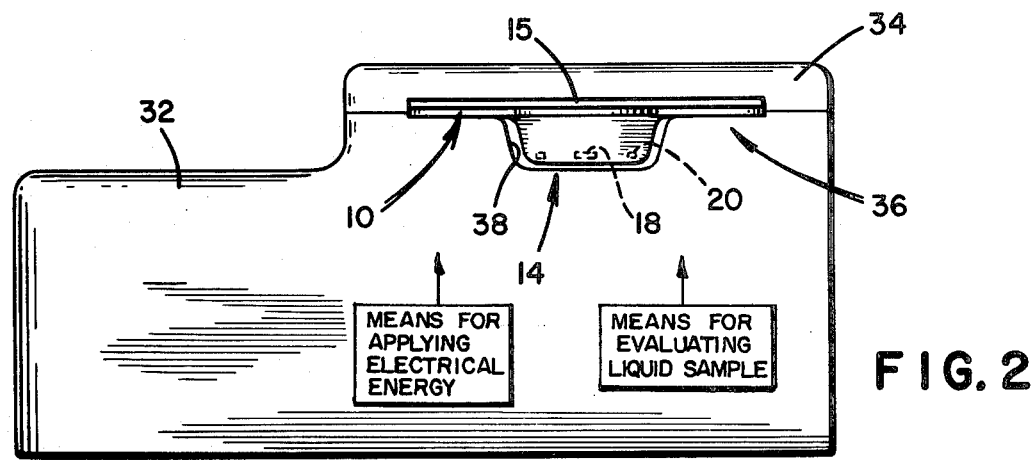
FIG. 2 is a front view of an instrument associated with the inventive card illustrated in FIG. 1.
Figure 1:
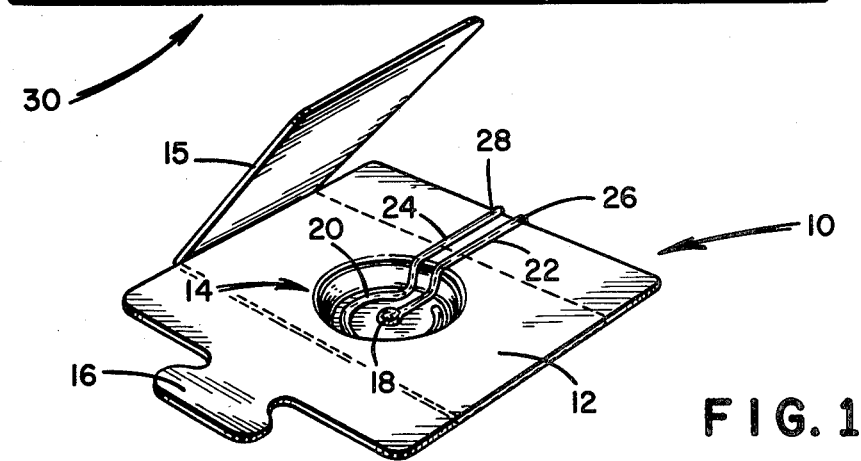
FIG. 1 is a perspective view of an inventive sample card.

With reference first to FIGS. 1 through 3, the first embodiment of the inventive sample card will be described. The sample card is shown generally at 10, and comprises a generally planar base portion 12 into which is recessed a central well 14. The well is preferably sized so as to accommodate approximately one drop of blood; a well volume on the order of 0.05 ml. is contemplated. A tab 16 extends from one edge of the card, and lies generally in the plane of base 12. The sample card 10 may be of many non-conductive materials, but for purposes of cost, ease of manufacture and suitabillity for disposal, a plastic is preferred.

An optional cover 15 is illustrated in FIG. 1, hinged at one surface of base 12. FIG. 2 illustrates cover 15 in its closed orientation. The purpose of cover 15 is to protect the clinician from disease; cover 15 also avoids loss of the sample.

A button electrode 18 is located in the central region of the well 14, and is encircled by an outer electrode 20. As seen best in FIG. 3, electrode 20 is generally hook-shaped, and is open at 21 to permit the passage of a lead 22 from button electrode 18. The outer electrode 20 is equipped with a similar lead 24.

The electrodes 18 and 20 are plated on the top interior surface of the well 14, and the associated electrode leads 22 and 24 are similarly plated on the upper surface of base 12. The respective electrode leads 22 and 24 extend to the edge of the base 12, as shown at 26 and 28.

An instrument, such as one for determining hematocrit, is shown generally at 30 in FIGS. 2 and 3. The instrument 30 has a base 32 and a top 34, and is provided with an intermediate groove, or track, 36, between the base and top. As seen best in FIG. 2, the groove 36 is shaped and dimensioned to accommodate the sample card 10, and includes a recess 38 compatible with the well 14.

The card 10 is held by tab 16 and is introduced to the instrument 30 by sliding the same into groove 36. When the card is fully introduced into instrument 30, the respectively electrode leads at 26 and 28 mate with spring contacts 40 and 42 of a conventional printed circuit connector device shown generally at 44.

In operation, the well 14 is filled with a sample to be tested, such as whole blood, and the card 10, with sample, is introduced into the instrument 30 by way of groove 36. Electrical contact is made between the leads on card 10 and the contacts of connector 44, and a current is passed through the sample. The conductivity of the sample is determined by measuring sample impedance, through the means of appropriate and conventional electronics (not shown). For example, if the instrument 30 were of the type used in hematocrit determinations, circuitry such as that disclosed in U.S. Pat. No. 3,922,598 could be employed.

With reference now to FIGS. 4 and 5, the second embodiment of the inventive sample card will be disclosed. In this embodiment, the sample card can be seen at 50, and includes a base 12, well 14 and tab 16 as previously described. This embodiment differs from the first in that the outer electrode, shown at 52, is in the form of a closed circle. The circular electrode 52 is plated on the upper surface well 14, and is integral with a lead 54 plated on the upper surface of base 12. The central electrode, illustrated at 56, is also different in this embodiment. Here, the lead 58 of the central electrode 56 is plated on the bottom surface of well 14 and base 12. As seen best in FIG. 5, the electrode 56 takes the form of a rivet in electrical contact with lead 58, and passing through the base of well 14 from the bottom into the interior thereof. This arrangement of central electrode 56 is adapted to enable the outer electrode to form a closed circle.

A third embodiment of the inventive sample card is shown in FIGS. 6 and 7 at 60. Here, like the embodiment described when reference was made to FIGS. 4 and 5, and outer electrode forms a closed circle about an inner electrode. In this embodiment, an inner electrode 64 comprises a button which passes through the base of the well 14, and an outer electrode 62 is plated on the upper surface of well 14 and forms a circle about inner electrode 64. A contact button 66, like button 64, is electrically integral with outer conductive 62, and passes through the base of the well 14.

Rigid connector pins 68 and 70, integral with respective buttons 64 and 66, extend from the bottom of the well 14, and serve to associate the electrodes of sample card 60 with the electronics of the instrument 30. These pins 68 and 70, as shown in FIG. 7, are able to mate with sockets 72 and 74, respectively, if the card 60 is introduced in the direction of arrow 75. In this case, the top of the instrument is open to accept the sample card 12. It should be understood, however, that other instrument-associated electrical contacts can be used. For example spring-like connectors could be employed to make contact with respective pins 68 and 70 if the card 60 were to be slid into the instrument 30 in a direction perpendicular to that represented by arrow 75.

Above, specific embodiments of the present invention have been described. It should be appreciated, however, that these embodiments were described for purposes of illustration only, without any intention of limiting the scope of the present invention. Rather, it is the intention that the present invention be limited only as is defined in the appended claims.

We claim:

1. A sample card for electrically operating on a liquid sample, the card comprising: a substantially planar base portion; a well portion extending out of said base portion so as to leave a substantially planar region completely surrounding said well portion; first electrode means in said well portion; second electrode means in said well portion, spaced and insulated from said first electrode means; first and second electrical leads electrically integral with said first and second electrode means, respectively, and connector means electrically integral with each of said first and second electrical leads, wherein said first electrode means is a button electrode located in the central region of said well portion; and wherein said second electrode means is a ring electrode extending substantially entirely around said first electrode means.

2. The sample card recited in claim 1, wherein said first and second electrode means are plated on said sample card.

3. The sample card recited in claim 1, wherein the respective first and second electrical leads are positioned on the same surface of said base portion.

4. The sample card recited in claim 1, wherein said second electrode means forms a complete circle about said first electrode means.

5. The sample card recited in claim 4, wherein the respective first and second electrical leads are positioned on opposite surfaces of said base portion.

6. The sample card recited in claim 4, wherein said first and second electrode means are electrically integral with respective button members extending through the surface of said well portion.

7. The sample card recited in claim 6, wherein said connector means comprise contact pins electrically integral with each of the respective button members, extending out of said surface of said well portion.

8. The sample card recited in claim 1, wherein said connector means are adapted to mate with associating connectors when the sample card is advanced in a direction perpendicular to the plane of said base portion.

9. The sample card recited in claim 1, wherein said connector means are adapted to mate with associating connectors when the sample card is advanced in a direction in the plane of said base portion.

10. The sample card recited in claim 1, and further comprising tab means integral with said base portion and generally in the plane thereof.

11. The sample card recited in claim 1, and further comprising cover means integral with said base portion for covering said well portion.

12. The sample card recited in claim 11, wherein said cover means is hinged to said base portion.

13. An apparatus for receiving a sample card having a generally planar base portion, a well portion extending out of the plane of said base portion, and spaced and insulated electrodes positioned in said well portion, said apparatus comprising: a base region; a top region; a groove intermediate said base and top region to accommodate the sample card; said groove including a track portion for receiving and guiding the base portion of the sample card, and a depression for accommodating the well of the sample card; electrical contact means for making electrical contact with the electrodes of the sample card; and means for evaluating an electrical characteristic of a liquid sample housed in the well of the sample card.

14. A prepackaged sterilized sample card for testing a body fluid, such as blood, the sample card comprising: a substantially planar base portion; tab means on said base portion for handling the sample card without contaminating the body fluid under test; a well region recessed into said base portion so as to leave a substantially planar region completely surrounding said well region for housing the body fluid under test; first and second spaced electrodes positioned within said well region for acting on the body fluid under test when in said well region; and first and second contact means electrically integral with said first and second electrodes, respectively, for applying an electrical signal to the body fluid under test, through said first and second electrodes.

15. The sample card recited in claim 14, wherein said first and second contact means serve to conduct electrical information from the body fluid under test for the purpose of evaluating a characteristic of said body fluid.

16. In combination, a sample card having a base portion, a well portion, formed in said base portion, first and second spaced and insulated electrode means in said well portion, and first and second electrical leads electrically integral with said first and second electrode means for electrically energizing said first and second electrode means; and an instrument having a main casing in which is carved a groove including a track portion for receiving and guiding the base portion of the sample card, and a depression for accommodating the well portion of the sample card, electrical contact means for making electrical contact with said first and second electrical leads, means for applying electrical energy to said contact means, and means for evaluating an electrical characteristic of a liquid sample housed in said well portion.

17. A sample card for electrically operating on a liquid sample, the card comprising: a substantially planar base portion; a well portion extending out of said base portion so as to leave a substantially planar region completely surrounding said well portion; first electrode means in said well portion; second electrode means in said well portion, spaced and insulated from said first electrode means; and connector means comprising first and second contact pins electrically integral with each of said first and second electrical leads, said contact pins extending out of said surface of said well portion and substantially perpendicular to the plane of said base portion.

18. A sample card for electrically operating on a liquid sample, the card comprising: a base portion; a well portion extending out of said base portion so as to leave a substantially planar region completely surrounding said well portion; first electrode means in said well portion; second electrode means in said well portion, spaced and insulated from said first electrode means; first and second electrical leads electrically integral with said first and second electrode means, respectively, and connector means electrically integral with each of said first and second electrical leads, wherein said first electrode means is a button electrode located in the central region of said well portion; and wherein said second electrode means is an electrode extending substantially entirely around said first electrode means.

19. A sample receptacle for electrically operating on a liquid sample, the receptacle comprising:
a substantially planar base portion made of an electrically insulating material;
a well portion defined by said base portion so as to leave a substantially planar region completely surrounding said well portion;
a first electrode in said well portion;
a second electrode in said well portion, spaced and insulated from said first electrode;
first and second electrical leads electrically connected with said first and second electrodes respectively, said first and second electrical leads extending from said first and second electrodes and defining contact portions to which electrical connection can be made.

20. A sample receptacle as claimed in claim 19, wherein said well has a volume substantially equivalent to the volume of one drop of blood.

21. A sample receptable as claimed in claim 19, wherein said well has a volume substantially 0.05 ml.

* * * * *